United States Patent
Lopez et al.

(10) Patent No.: US 7,753,582 B2
(45) Date of Patent: Jul. 13, 2010

(54) THERMAL CONDUCTIVITY SENSOR

(75) Inventors: Martin Lopez, Rotherfield (GB); James Hobby, Crowborough (GB); Bahram Alizadeh, Maidstone (GB); Richard P. Kovacich, Crowborough (GB)

(73) Assignee: Servomex Group Limited, East Sussex (GB)

( * ) Notice: Subject to any disclaimer, the term of this patent is extended or adjusted under 35 U.S.C. 154(b) by 117 days.

(21) Appl. No.: 11/687,760

(22) Filed: Mar. 19, 2007

(65) Prior Publication Data

US 2007/0223558 A1 Sep. 27, 2007

(30) Foreign Application Priority Data

Mar. 21, 2006 (GB) ................................. 0605683.2

(51) Int. Cl.
- *G01N 25/18* (2006.01)
- *G01K 17/00* (2006.01)
- *G01K 1/00* (2006.01)
- *G01K 7/00* (2006.01)

(52) U.S. Cl. ......................... 374/44; 374/208; 374/185; 374/10; 374/31

(58) Field of Classification Search .................. 374/44, 374/185, 10, 208, 31
See application file for complete search history.

(56) References Cited

U.S. PATENT DOCUMENTS

| | | | |
|---|---|---|---|
| 3,084,536 A | 4/1963 | McNabb | |
| 3,097,518 A | 7/1963 | Taylor et al. | |
| 3,474,660 A | 10/1969 | Dooley | |
| 3,777,366 A | 12/1973 | Kiefer | |
| 4,215,564 A | 8/1980 | Lawson et al. | |
| 4,735,082 A * | 4/1988 | Kolloff | 73/25.03 |
| 4,850,714 A * | 7/1989 | Wiegleb | 374/44 |
| 4,944,035 A * | 7/1990 | Aagardl et al. | 702/136 |

(Continued)

FOREIGN PATENT DOCUMENTS

CN   101042359 A   9/2007

(Continued)

OTHER PUBLICATIONS

"Standard Test Method for Thermal Conductivity of Liquids'" ANSI Designation D2717-95 (Reapproved 2005); TIB Hannover +495117682998; Jan. 1995; pp. 1101-1104.

(Continued)

*Primary Examiner*—Gail Verbitsky
*Assistant Examiner*—Mirellys Jagan
(74) *Attorney, Agent, or Firm*—Daly, Crowley, Mofford & Durkee, LLP

(57) ABSTRACT

A sensor for determining the thermal conductivity of a fluid comprising a sensing module located within a housing having inlet and outlet ports for a fluid under test, the sensing module comprising a reference base surface and a sensing element spaced therefrom and having measure and reference sections, and there being provided electrical power monitoring means for monitoring the power through the measure and reference sections in order to generate a signal indicative of the power difference due to thermal conductivity through the fluid. The sensing element is a thick film printed disc with measure and reference resistors printed on it. All changes in the fluid are common to both the measure and reference sections except for the thermal conductivity of the fluid itself.

15 Claims, 2 Drawing Sheets

U.S. PATENT DOCUMENTS

| | | | | |
|---|---|---|---|---|
| 5,038,304 | A * | 8/1991 | Bonne | 702/99 |
| 5,177,696 | A * | 1/1993 | Bonne | 702/136 |
| 5,251,980 | A * | 10/1993 | Hiraoka et al. | 374/7 |
| 5,311,447 | A * | 5/1994 | Bonne | 702/50 |
| 5,335,993 | A * | 8/1994 | Marcus et al. | 374/11 |
| 5,756,878 | A * | 5/1998 | Muto et al. | 73/25.03 |
| 5,772,321 | A * | 6/1998 | Rhodes | 374/44 |
| 6,019,505 | A * | 2/2000 | Bonne et al. | 374/40 |
| 6,132,083 | A * | 10/2000 | Enala | 374/44 |
| 6,169,965 | B1 * | 1/2001 | Kubisiak et al. | 702/136 |
| 6,361,206 | B1 * | 3/2002 | Bonne | 374/138 |
| 6,428,203 | B1 * | 8/2002 | Danley | 374/10 |
| 6,497,509 | B2 * | 12/2002 | Merzliakov et al. | 374/44 |
| 6,701,774 | B2 * | 3/2004 | Srinivasan et al. | 73/23.42 |
| 7,003,418 | B2 * | 2/2006 | Bonne et al. | 702/100 |
| 7,350,971 | B2 * | 4/2008 | Egolf et al. | 374/44 |
| 2001/0032503 | A1 * | 10/2001 | Schrittenlacher | 73/204.11 |
| 2002/0085615 | A1 * | 7/2002 | Nakamura et al. | 374/12 |
| 2004/0099057 | A1 | 5/2004 | Hornung et al. | |
| 2004/0250601 | A1 | 12/2004 | Lin | |
| 2005/0028580 | A1 * | 2/2005 | Bauer et al. | 73/25.03 |
| 2008/0025366 | A1 * | 1/2008 | McBurney | 374/44 |
| 2008/0291966 | A1 * | 11/2008 | Engel et al. | 374/29 |
| 2009/0016403 | A1 * | 1/2009 | Chen et al. | 374/45 |
| 2010/0046573 | A1 * | 2/2010 | Schick et al. | 374/11 |

FOREIGN PATENT DOCUMENTS

| | | |
|---|---|---|
| DE | 26 18 349 | 4/1976 |
| EP | 0 348 243 A2 | 12/1989 |
| EP | 0 348 243 A3 | 12/1989 |
| EP | 1 837 645 A2 | 9/2007 |
| EP | 1 837 645 A3 | 9/2007 |
| GB | 1024869 | 4/1966 |
| GB | 1143002 | 2/1969 |
| WO | WO 98/20314 A2 | 5/1998 |
| WO | WO 98/20314 A3 | 5/1998 |
| WO | WO 00/40953 | 7/2000 |

OTHER PUBLICATIONS

McConnell et al. "Variable Temperature Apparatus using a Thermal Conductivity Measurement Technique for the Determination of Superconducting AC Power Loss;" Review of Scientific Instruments, vol. 46, No. 5, May 1975; 6 sheets.

Great Britain Search Report dated May 5, 2006 for GB0605683.2 filed on Mar. 21, 2006.

European Search Report dated Jun. 18, 2009 for EP07251159.5 filed on Mar. 20, 2007.

European Examination Report dated Jun. 18, 2009 for EP07251159.5 filed on Mar. 20, 2007.

Servomex Group Ltd.; GB Patent Application No. GB 0605683.2 filed on Mar. 21, 2006; 14 sheets (parent application).

* cited by examiner

THERMAL CONDUCTIVITY SENSOR

CROSS REFERENCE TO RELATED APPLICATIONS

This application claims priority under 35 U.S.C. §119 to Great Britain patent application No. GB 0605683.2 filed on Mar. 21, 2006, which is incorporated herein by reference.

DETAILED DESCRIPTION OF THE INVENTION

A novel sensor is presented for determining the thermal conductivity of a fluid. The basic time independent equation for thermal conductivity between two surfaces of area A, separated by a medium of thermal conductivity K is given in equation (1) below:

$$K = \frac{P}{A\left(\frac{dT}{dx}\right)} \quad (1)$$

where P is the power dissipated through thermal conductivity and dT/dx is the thermal gradient with distance between the two surfaces.

Therefore a simple way to determine the thermal conductivity of a fluid is to measure the power required to maintain a defined thermal gradient where A is known and the other loss mechanisms are defined. K can also be measured in the time domain where the thermal gradient is changing with time. The change in the thermal conductivity with fluid composition for binary or pseudo-binary mixtures can also be used to determine the concentration of the components, provided that the components have different thermal conductivities and that the system has been calibrated or that the component thermal conductivities are known.

This simple arrangement can be used to measure thermal conductivities, but is subject to sensitivity limitations due to background effects such as ambient temperature fluctuations and convective or flow effects. Efforts to minimise convective effects through designs to have purely diffusion driven systems have the disadvantage of poor time response. The use of a sealed reference element in a stable medium (normally the zero calibration gas) can be used to negate the effect of temperature changes in the housing, but this must be precisely matched to the measure element and cannot compensate for flow or convective effects experienced by the measure element.

The present invention uses a sensor design whereby both measurement and reference sections of the element are held within substantially the same environment, such that all changes in the fluid are common to both measure and reference sections, except for the thermal conductivity properties of the fluid itself. This allows for common mode rejection of background noise, thus enhancing the performance of the sensor.

In order that the present invention be more readily understood, an embodiment thereof will now be described by way of example with reference to the accompanying drawings, in which.

Figure 1:
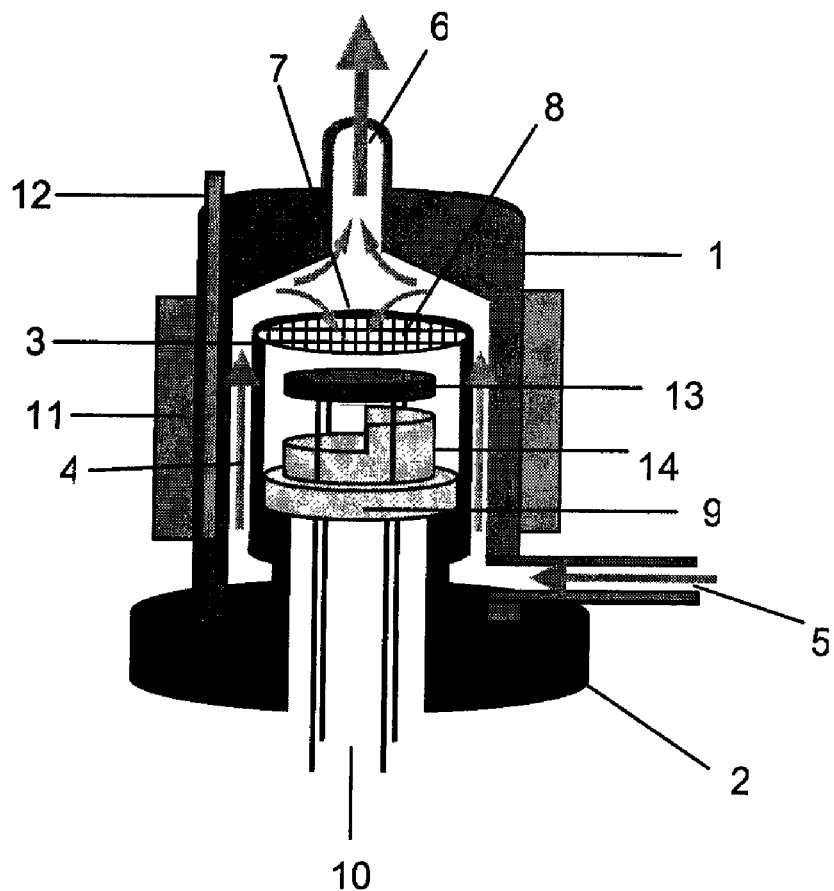
FIG. 1 shows a diagrammatic view of part an embodiment of the present invention.

The preferred embodiment of sensor comprises an inverted cup-shaped housing 1 having an open end located on a base member 2. A tubular shroud 3 is located within the housing 1 so as to form an annular space 4 between the outer walls of the shroud 3 and the inner wall of the housing. The shroud 3 is shorter than the height of the housing 1 and is open topped.

Fluid to be monitored is introduced into the space 4 through an inlet port 5 in the housing and is exhausted through an outlet port 6 from the closed end of the housing 1. The closed end is shaped so as to promote diffusion of some of the fluid flow into the interior of the tubular shroud through its open end 7 which is spaced from the end of the housing 1.

A diffusive element 8 may be present to more precisely control the diffusion rate of the fluid through the open end of the shroud 7 and hence minimise any residual flow effects. A sensing module 9 is located within the tubular shroud and electrical connections 10 to the module 9 are achieved through an aperture in the base member 2.

The fluid in the space 4 has its temperature maintained stable by means of a heater 11 which is shown as being located in the exterior of the housing in the region of the space 4. A temperature sensor 12 is provided for monitoring the temperature of the fluid into space 4.

The housing 1 is designed to pre-heat the fluid, if required, maintain a uniform temperature and to provide a flow environment which is substantially diffusion driven by the time the fluid reaches the sensing module 9. The sensing module consists of a disc 13 mounted at a defined height from a base 14, which is also maintained at a stable temperature. The disc 13 is held within a cylindrical oven, whose symmetry further enhances the common mode environment between the measure and reference sections of the disc.

Figure 2:
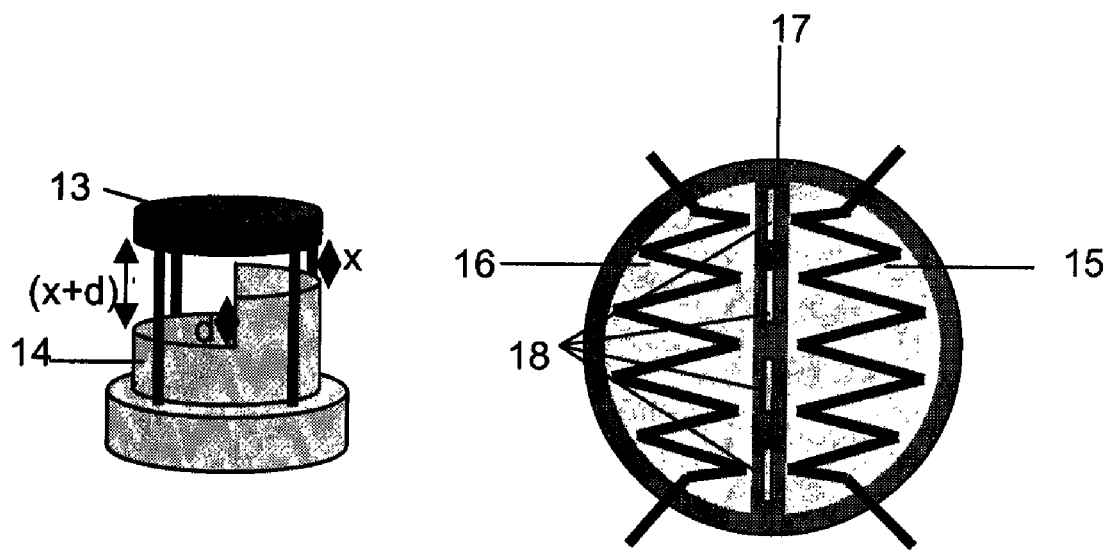
FIG. 2 shows a diagrammatic view of a part of the embodiment shown in FIG. 1, together with a plan view of a thick film printed disc.

A close-up view of the sensing module is shown in FIG. 2. The sensing element is shown as a thick film printed disc 13 containing measure and reference sections 15,16 (identical platinum resistors) mounted on a common planar platform in the form of a ceramic substrate 17, but could equally well be composed of multiple elements, a thin film structure, precision resistors, thermistors or other thermal elements. Thermal breaks 18 are provided in the substrate between the measure and reference sections 15, 16.

There is a difference (d) in the distance between the measure section of the disc 15 and base 14 (x) and the reference section of the disc 16 and the base 14 (x+d). This difference could be created by a step or out-dent in the surface of the disc or base and/or by creating an indent or by other means. The two halves of the disc are held at the same temperature above the base temperature by passing current through identical resistive elements printed on the substrate material, thus minimising thermal leaks between the measurement 15 and reference 16 sections. Any thermal leaks between the two half sections due to any residual imbalance in temperature can be further minimised by selection of a substrate material with low thermal conductivity and the use of thermal breaks 18.

The thermal conductivity K can be determined using equation 1 as:

$$K = \frac{(P_M - P_R)x(x+d)}{A(T_D - T_B)d} \quad (2)$$

where $P_M$ is the power dissipated through thermal conductivity through the fluid for the measure section, $P_R$ is the power dissipated through thermal conductivity through the fluid for the reference section, A is the surface area for the measure and reference sections of the disc (half the area of the disc), $T_D$ is the temperature of the disc (both measure and reference sections), $T_B$ is the temperature of the base, x is the distance between the measuring element and the base and d is the step height in the base. The distance x is kept small compared the disc radius to enhance the sensitivity by the thermal conductivity losses through the medium to the base and to maintain a small diffusion volume. Likewise, the step height d should be sufficient to provide the required sensitivity, whilst still maintaining a similar environment to that experienced by the measure section.

Figure 3:
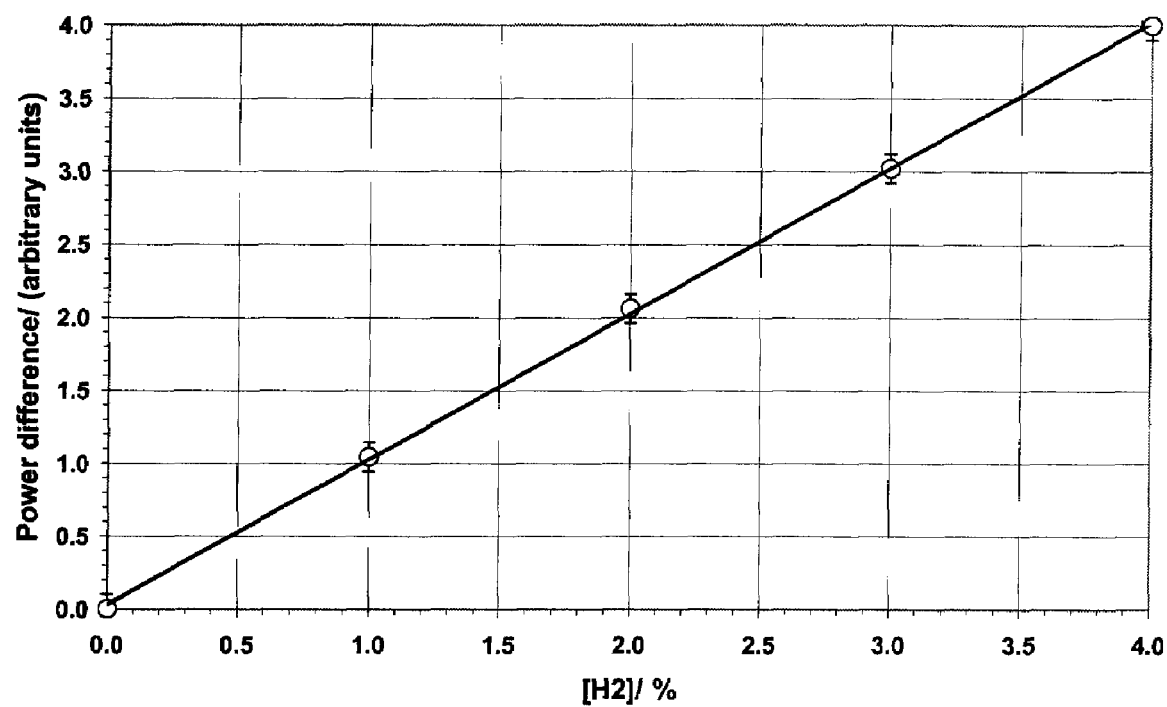
FIG. 3 shows a graph of power difference against thermal conductivity for the embodiment.

FIG. 3 illustrates measurements taken using the above embodiment with platinum resistor tracks printed on an yttria stabilised zirconia disc with thermal slots present. The graph shows that the signal (power difference) is proportional to the hydrogen concentration for a hydrogen/nitrogen gas mixture. Since the thermal conductivities of pure hydrogen and nitrogen gases differ substantially (hydrogen being larger), increasing levels of hydrogen increase the thermal conductivity of the fluid mixture and hence the concentration of hydrogen in the mix can be established if the sensor has been calibrated using known standards.

Since the measure and reference sections experience substantially the same environment, except for the thermal conductivity losses through the fluid to the base, most of the noise which would be experienced by just using a single measuring element is now rejected as common mode with the reference. The open structure above the disc and small diffusion volume beneath the disc allow a quick inter-change time when the fluid composition changes and hence a fast flush time. This principle could be used with multiple measuring and reference elements in order to obtain an averaged signal and the measurement itself could take place as a steady state measurement or with a changing temperature and/or distance of the disc from the base with time and could be used with heat being added, such as by a resistive element or with heat being taken away, such as with a Peltier cooler.

A similar result could be obtained if the measure and reference sections of the disc were held at the same temperature above a flat base, but with the two corresponding halves of the base held at different temperatures. An alternative embodiment could also be made with the two sections of the disc held at different temperatures with a flat or stepped base maintained at a controlled temperature in order to create different thermal gradient between the measure and reference sections of the disc and the base. This could also be achieved using multiple elements and/or in the steady state or time domain.

The sensing element could also be run as a Wheatstone bridge. In this case, the preferred embodiment could be used as before, but this time, two external resistors could be used to create a full bridge. The measure and reference sections of the disc make up one arm of the bridge and the external reference resistors the other arm. A full Wheatstone bridge could also be printed onto the disc with the measure and reference resistors arranged either on quadrants of the disc or on each half. The current flowing in the bridge causes the disc to heat up above the ambient temperature. The temperatures of the measure and reference sections of the disc are no longer identical and will be related to the thermal conductivity losses through the medium to the base. The output voltage signal which is related to the difference in temperature between the measure and reference sections of the disc is also therefore related to the thermal conductivity of the medium. Thermal leaks between the two half sections will reduce the sensitivity and can be minimised by selection of a thin substrate material with low thermal conductivity and the use of thermal breaks.

The Wheatstone bridge could be run in constant voltage, constant current or constant resistance mode. It could be also run in a modified Wheatstone bridge mode, where the extra power applied to the measure and/or reference elements to maintain a fixed voltage offset could be used to determine the thermal conductivity of the medium.

The Wheatstone bridge could be run in direct current mode or alternating current mode with or without synchronous detection. The measure and reference sections could also be held at fixed temperatures or be allowed to vary their temperatures and/or distance from the base with time. As before, the equivalent measurement could be made using separate measure and reference elements rather than being on the same disc and using alternative thermal sources and/or detectors.

Another alternative arrangement would be to provide heating to the disc substrate via a thick film printed resistor or resistors and use a low power thick film printed Wheatstone bridge, electrically insulated from the heater resistor(s), to sense the localised thermal differences between the measure and reference sections due to the thermal conductivity losses through the medium.

A bridge could also be designed with a deliberate imbalance in resistances used for the measure and reference sections so as to create a temperature difference between the measure and reference sections and a flat or stepped base. The imbalance in resistances could also be used to minimise any temperature difference seen between the measure and reference sections where the distances to the base differs. This would help increase sensitivity and common mode rejection.

All references cited herein are hereby incorporated herein by reference in their entirety.

Having described preferred embodiments of the invention, it will now become apparent to one of ordinary skill in the art that other embodiments incorporating their concepts may be used. It is felt therefore that these embodiments should not be limited to disclosed embodiments, but rather should be limited only by the spirit and scope of the appended claims.

What is claimed is:

1. A sensor for determining the thermal conductivity of a fluid comprising a sensing module located within a housing having inlet and outlet ports for a fluid under test, the sensing module comprising a reference base surface and a sensing element spaced therefrom and having measure and reference sections, the sensor having means to provide electrical power and to control respective temperatures of the measure and reference sections relative to the base surface, and monitoring means for monitoring respective powers applied to the measure and reference sections in order to generate a signal indicative of a difference between magnitudes of the powers applied to the measure and reference sections resulting from thermal conductivity through the fluid.

2. The sensor according to claim 1, wherein the monitoring means includes a Wheatstone bridge, the output of which constitutes the generated signal.

3. The sensor according to claim 1, wherein a diffusive element is suitable for use to control the fluid diffusion rate onto the sensing element.

4. The sensor according to claim 1, wherein the sensing element is a thin film element.

5. The sensor according to claim 1, wherein a thermistor or Peltier cooler is used for the measure and reference sections of the sensing element.

6. The sensor according to claim 1, wherein multiple measure and reference sections are provided in the sensing element.

7. The sensor according to claim 1, wherein said base surface is a flat base surface.

8. The sensor according to claim 7, wherein a temperature difference is maintained between an area of the base surface below the measure section and an area of the base surface below the reference section.

9. The sensor according to claim 1, wherein the sensing element is a thick film printed disc with measure and reference resistors printed on it.

10. The sensor according to claim 2, wherein said sensing element includes a substrate having a substrate material of low thermal conductivity.

11. The sensor according to claim 10, wherein the sensing element is provided with thermal breaks between the measure and reference sections.

12. The sensor according to claim 1, wherein the measure and reference sections are held at the same temperature above the temperature of the base surface.

13. The sensor according to claim 12, wherein said base surface is a stepped base surface.

14. The sensor according to claim 13, wherein the measure and reference sections are located at different distances from the base surface below said sections.

15. The sensor according to claim 14, wherein there is a difference, d, in the distance, x, between the measure section and the base surface and the distance, x+d, between the reference section and the base surface.

* * * * *

UNITED STATES PATENT AND TRADEMARK OFFICE
CERTIFICATE OF CORRECTION

| | | |
|---|---|---|
| PATENT NO. | : 7,753,582 B2 | Page 1 of 1 |
| APPLICATION NO. | : 11/687760 | |
| DATED | : July 13, 2010 | |
| INVENTOR(S) | : Martin Lopez et al. | |

It is certified that error appears in the above-identified patent and that said Letters Patent is hereby corrected as shown below:

Title Page, line (75), delete "Inventors: Martin Lopez, Rotherfield (GB); James Hobby, Crowborough (GB); Bahram Alizadeh, Maidstone (GB); Richard P. Kovacich, Crowborough (GB)" and replace with -- Inventors: Martin Lopez, East Sussex (GB); James Hobby, East Sussex (GB); Bahram Alizadeh, Kent (GB); Richard P. Kovacich, East Sussex (GB) --.

Col. 1, line 63, delete "of part on" and replace with -- of a part of an --.

Col. 2, line 3, delete "of sensor" and replace with -- of the sensor --.

Col. 3, line 6, delete "compared the" and replace with -- compared to the --.

Col. 3, line 46, delete "create different" and replace with -- create a different --.

Signed and Sealed this
Fifth Day of April, 2011

David J. Kappos
*Director of the United States Patent and Trademark Office*